United States Patent [19]
Colella et al.

[11] Patent Number: 6,003,006
[45] Date of Patent: *Dec. 14, 1999

[54] SYSTEM OF DRUG DISTRIBUTION TO HEALTH CARE PROVIDERS

[75] Inventors: Salvatore J. Colella, New Kensington, Pa.; Stephen M. Lawrence, Lexington, Ky.; Gerald J. Widenhofer, Dublin, Ohio

[73] Assignee: Pyxis Corporation, San Diego, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/762,041

[22] Filed: Dec. 9, 1996

[51] Int. Cl.$^6$ .................................................. G06F 17/60
[52] U.S. Cl. .......................................... 705/2; 364/479.07
[58] Field of Search ................................... 705/2, 26, 28, 705/29, 30, 34, 14, 8; 364/479.07

[56] References Cited

U.S. PATENT DOCUMENTS

| | | | |
|---|---|---|---|
| 5,406,475 | 4/1995 | Kouchi et al. | 705/8 |
| 5,611,051 | 3/1997 | Pirelli | 705/28 |
| 5,682,728 | 11/1997 | DeBusk et al. | 705/29 |
| 5,694,551 | 12/1997 | Doyle et al. | 705/26 |
| 5,712,989 | 1/1998 | Johnson et al. | 705/29 |
| 5,713,485 | 2/1998 | Liff et al. | 221/2 |

*Primary Examiner*—Emanuel Todd Voeltz
*Assistant Examiner*—Thomas A. Dixon
*Attorney, Agent, or Firm*—Michael D. Steffensmeier

[57] ABSTRACT

A system and method are described in which a drug distribution center operates a computer software drug inventory management program in electronic communication with a health care provider computer software program for drug distribution to patients. The system and method preferably incorporate low unit dose measure drug packaging including bar codes. The bar codes may be scanned into either software program for automatically tracking such information as drug lot numbers and expiration dates.

20 Claims, 8 Drawing Sheets

SYSTEM OF DRUG DISTRIBUTION TO HEALTH CARE PROVIDERS

BACKGROUND AND SUMMARY OF THE INVENTION

The present invention relates generally to a system for drug distribution to health care providers, and more particularly, the present invention relates to a system for drug information transfer, drug inventory management, and drug packaging, resulting in a unique system of drug distribution.

It has been known for health care providers, such as hospitals, to have a pharmacist or pharmacy department within the hospital to coordinate the dispensing of drugs to the patients of the health care institution. The pharmacists in such health care institutions have long been burdened with the increasingly complex record keeping and inventory management that results from hospitals caring for hundreds, if not thousands of patients every day. Various methods have been employed to assist a hospital's pharmacist or pharmacy department with maintaining accurate records while attempting to reduce the burden of managing all of the information associated with drug distribution. The pharmacist's responsibility has included: filling individual patient prescriptions on a daily basis; maintaining sufficient inventory of each drug in order to have enough quantities of the drug in hospital stock to administer to patients on a daily basis; tracking of drug interactions to prevent a patient from being given a drug that has adverse affects when combined with other drugs; accounting for the purchase of drugs for use in the hospital; accounting associated with the giving of drugs to individual patients; distributing the drugs to the appropriate nursing stations within the hospital to suit each station's daily demands; tracking of drug expiration dates to rid inventories of expired drugs; and tracking of drug lot numbers, for example in the event of a recall of a particular drug.

In recent years hospitals have been assisted with drug distribution management by the introduction of drug dispensing machines, such as the machines described in U.S. Pat. No. 5,014,875, entitled, Medication Dispenser Station and U.S. Pat. No. 5,460,294, entitled, Single Dose Pharmaceutical Dispenser Subassembly. Drug dispensing machines have effectively created branches of the hospital pharmacy department at each nursing station where the dispensing machines are located. The dispensing machines are frequently arranged to be electronically connected to a central computer system within the pharmacy department for tracking drugs that were to be administered to patients in that particular patient care area of the hospital. In this manner, hospitals have improved the manner in which drugs are dispensed to patients and the record keeping required by the pharmacy department has been simplified somewhat by each patient care area electronically reporting the variety and quantities of drugs dispensed from each drug dispensing machine.

Health care providers, such as hospitals, have traditionally purchased drugs from drug distributors, in bulk quantities (e.g., 100 single dose units of a particular variety of drug). While hospitals have purchased drugs in bulk due to manufacturer availability and then offered by the drug distributor, drugs are nevertheless dispensed at the health care institution on a patient-by-patient basis in low dose quantities. Therefore, hospitals have had to purchase and maintain large quantities of drugs until the drugs were eventually dispensed to the patients. Inventory turnover of drugs is usually measured in days, weeks or more. During such time, the hospitals have had to incur the associated expense of carrying this large inventory of drugs. Frequently, the result has been independent management of such large quantities, including unexplained loss of portions of the drugs in inventory, and even theft of portions of the inventory. In addition, the pharmacy department of the hospital has had the extra burden of tracking the drugs dispensed for patient use, as well as tracking the drugs that the pharmacy is carrying in its inventory.

The present invention is designed to overcome several of the above mentioned problems associated with health care provider drug distribution. The present invention includes a unique form of drug packaging in combination with a computerized drug management software system. Low unit of measure quantities of a drug are packaged in an enclosure, such as a sealed plastic bag, and the bag is preferably marked with a lot number and a related lot number bar code for tracking the lot from which the drugs within that particular package were taken. The package may also include an expiration date and related expiration date bar code for tracking the expiration date of the drugs within the package. The package may also include an National Drug Code ("NDC") number and related NDC number bar code for identifying the variety of drug packaged within the enclosure. The package may also include further information regarding its contents.

Once the drugs are packaged, they may be warehoused at a drug distribution center. When a health care provider requires drugs the drug distribution center delivers the low unit measure packages in accordance with the hospital's current needs. Once the low unit measure packages arrive at the hospital, the bar codes may be scanned by the hospital pharmacy to be automatically logged into the hospital's drug information management system in electronic communication with the drug distributor's management information system to track exactly what drugs and quantities arrived at the hospital in each shipment. Furthermore, the bar codes on the packages may be used to track the drugs that are placed in each drug dispensing machine at each patient care area within the hospital. The hospital's drug management information system will thus know the items placed in each drug dispensing machine in the hospital, including drug type, lot numbers, and expiration dates.

In addition, the present invention provides a computerized electronic interface between the hospital software system which tracks the drug distribution within the hospital and the drug distributor's software system at the drug distribution center warehouse. By enabling these two systems to communicate with each other, the system of the present invention provides a complete drug distribution management system from the warehouse to the patient care area within the hospital.

BRIEF DESCRIPTION OF THE DRAWINGS

Figure 6:
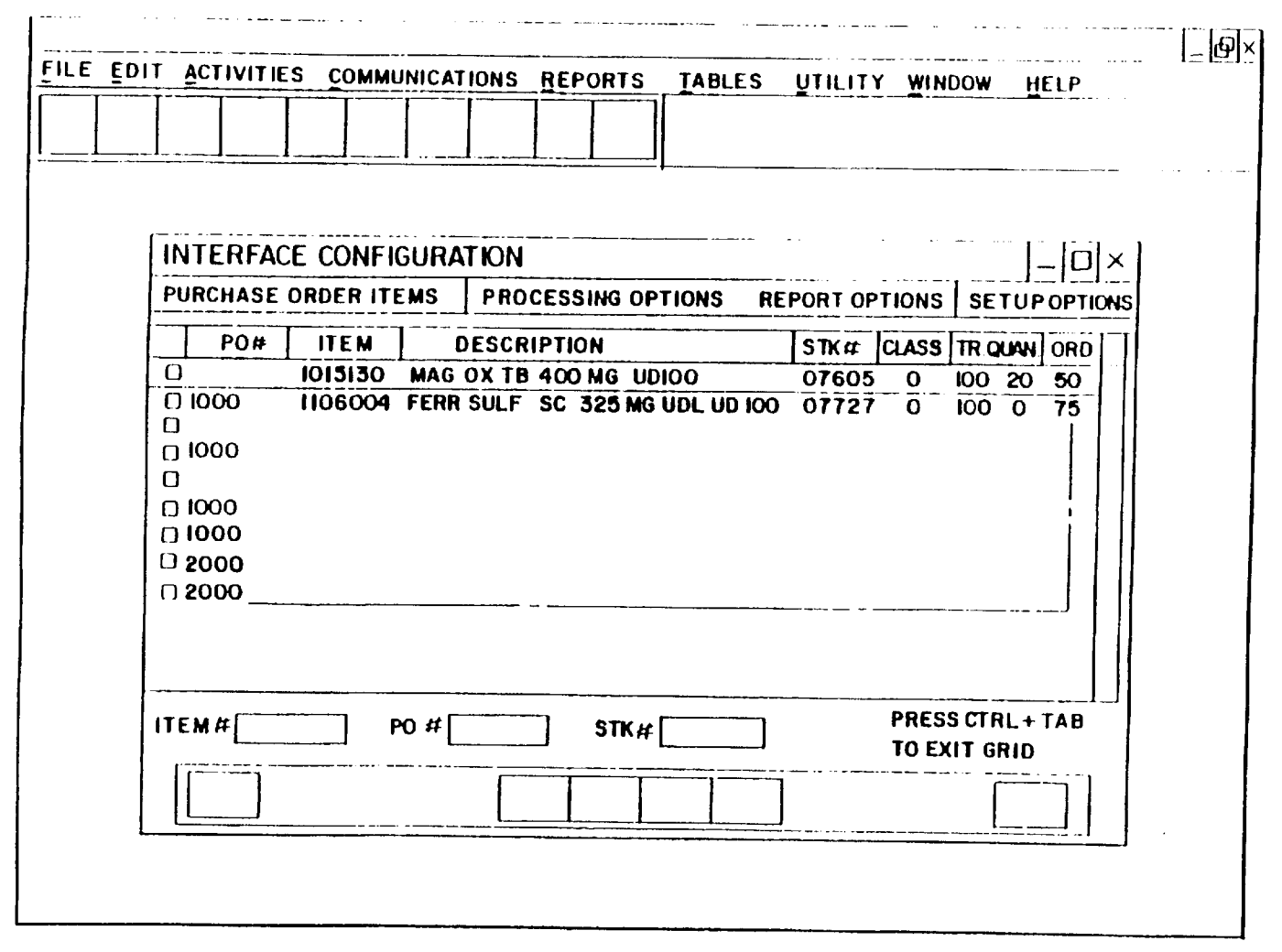

FIG. 6 shows an example data screen of a preferred form of the computer software system of the present invention.

DETAILED DESCRIPTION OF PREFERRED EMBODIMENT(S)

Figure 1A:
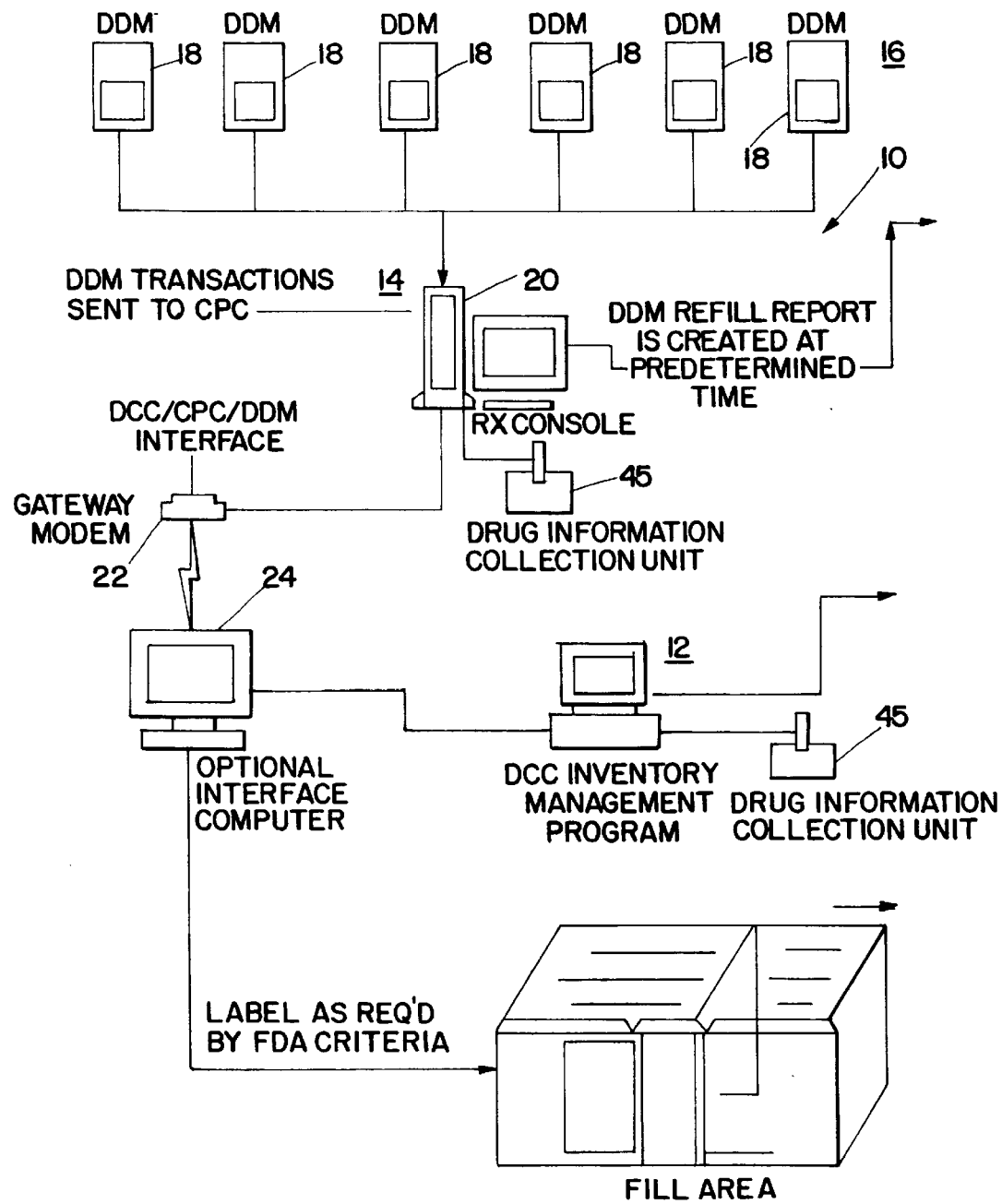
FIGS. 1A and 1B show a schematic diagram of a preferred embodiment of the system of the present invention.
Figure 1B:
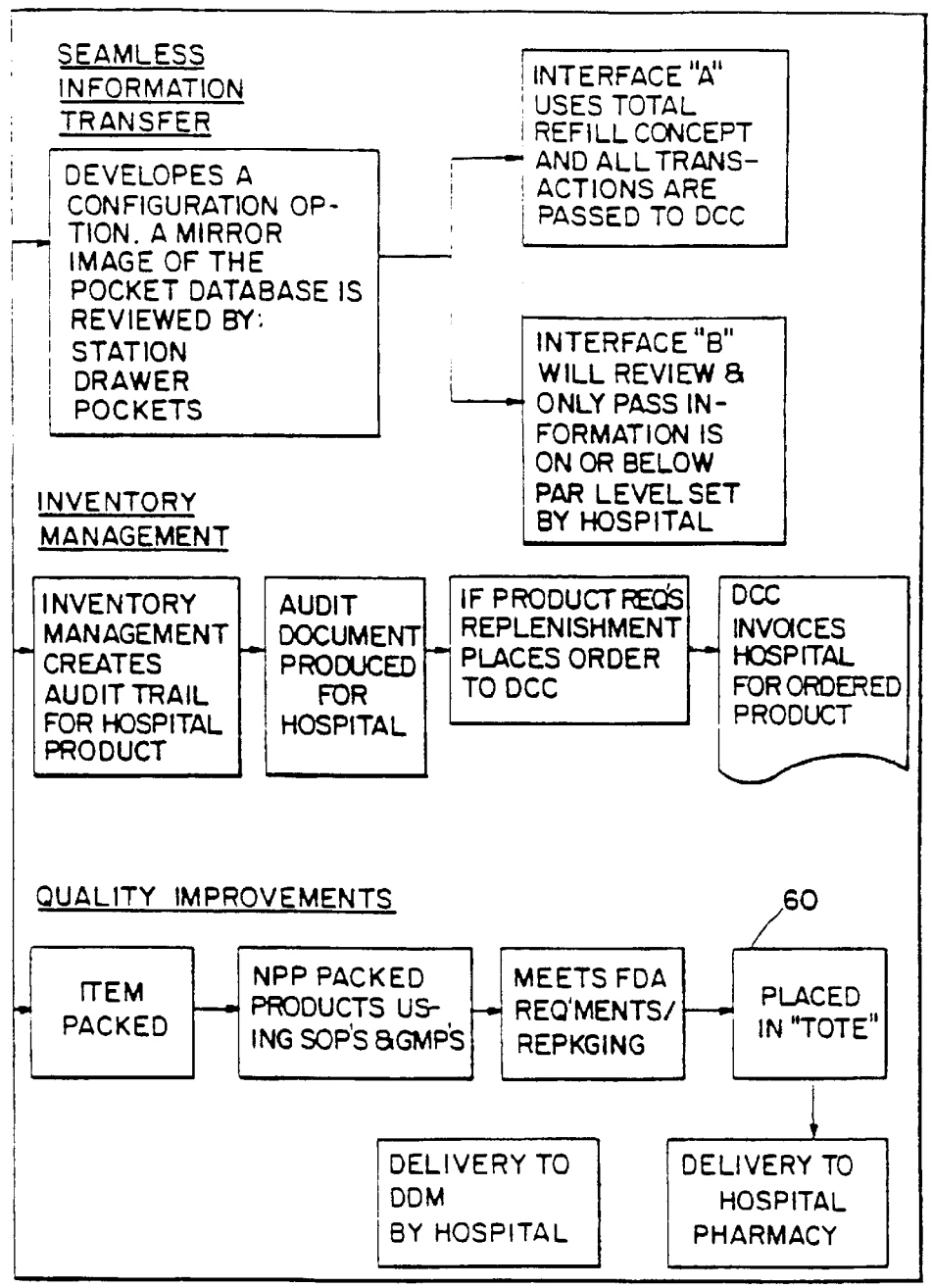
Figure 2:
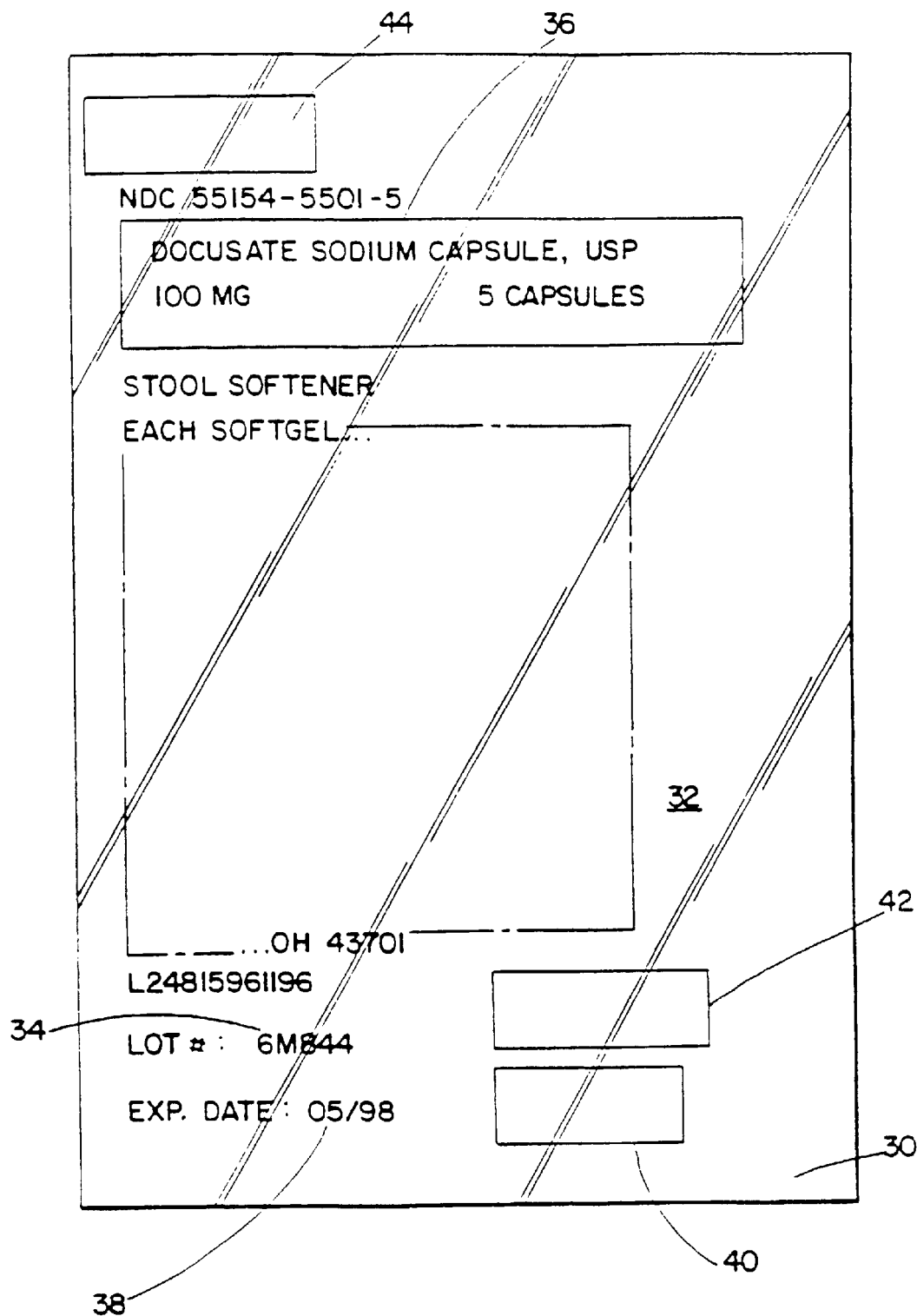
FIG. 2 shows an actual size of a face of a plastic bag for low unit measure drug packaging of one embodiment of the system of the present invention.
Figure 3A:
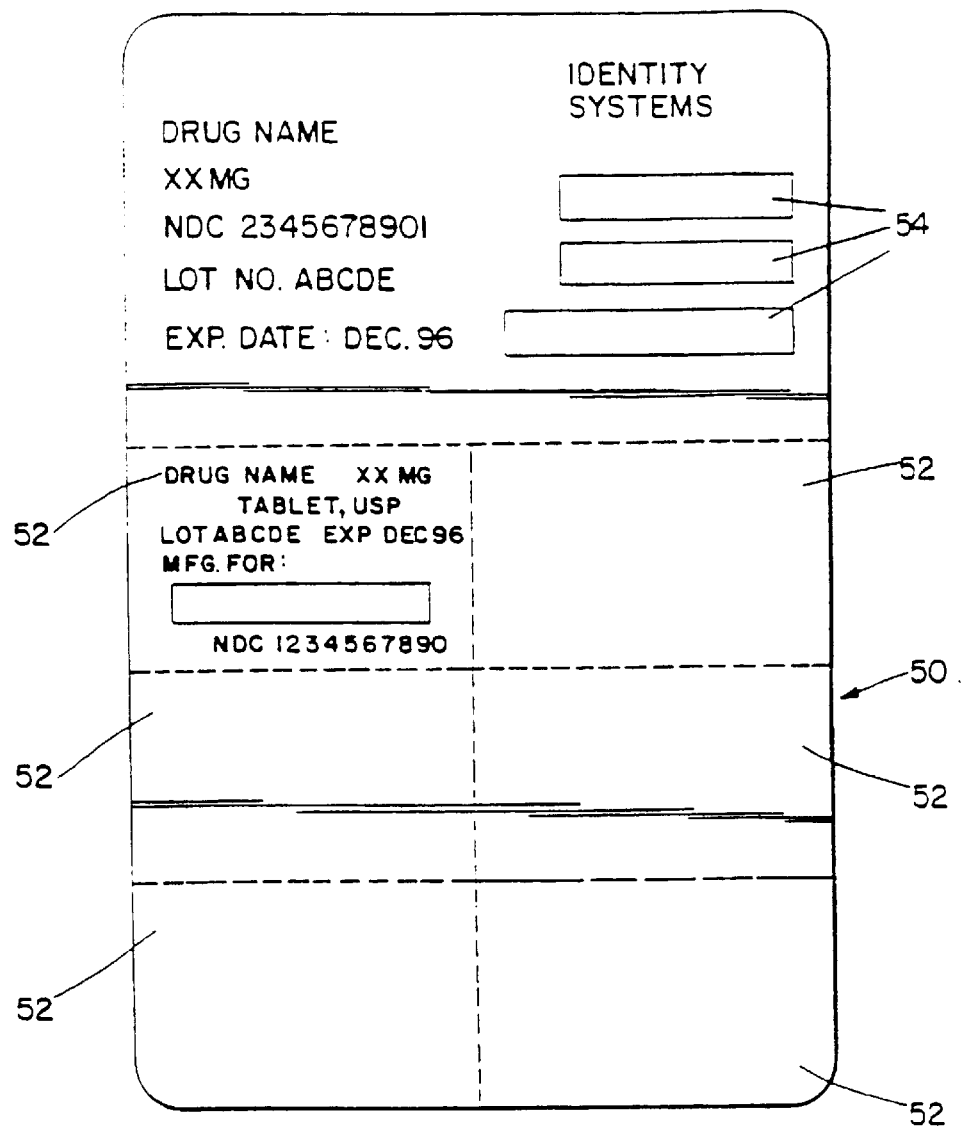
FIG. 3A shows an actual size of a face of a drug packaging card for low unit dose drug packaging of another embodiment of packaging for the system of the present invention.
Figure 3B:
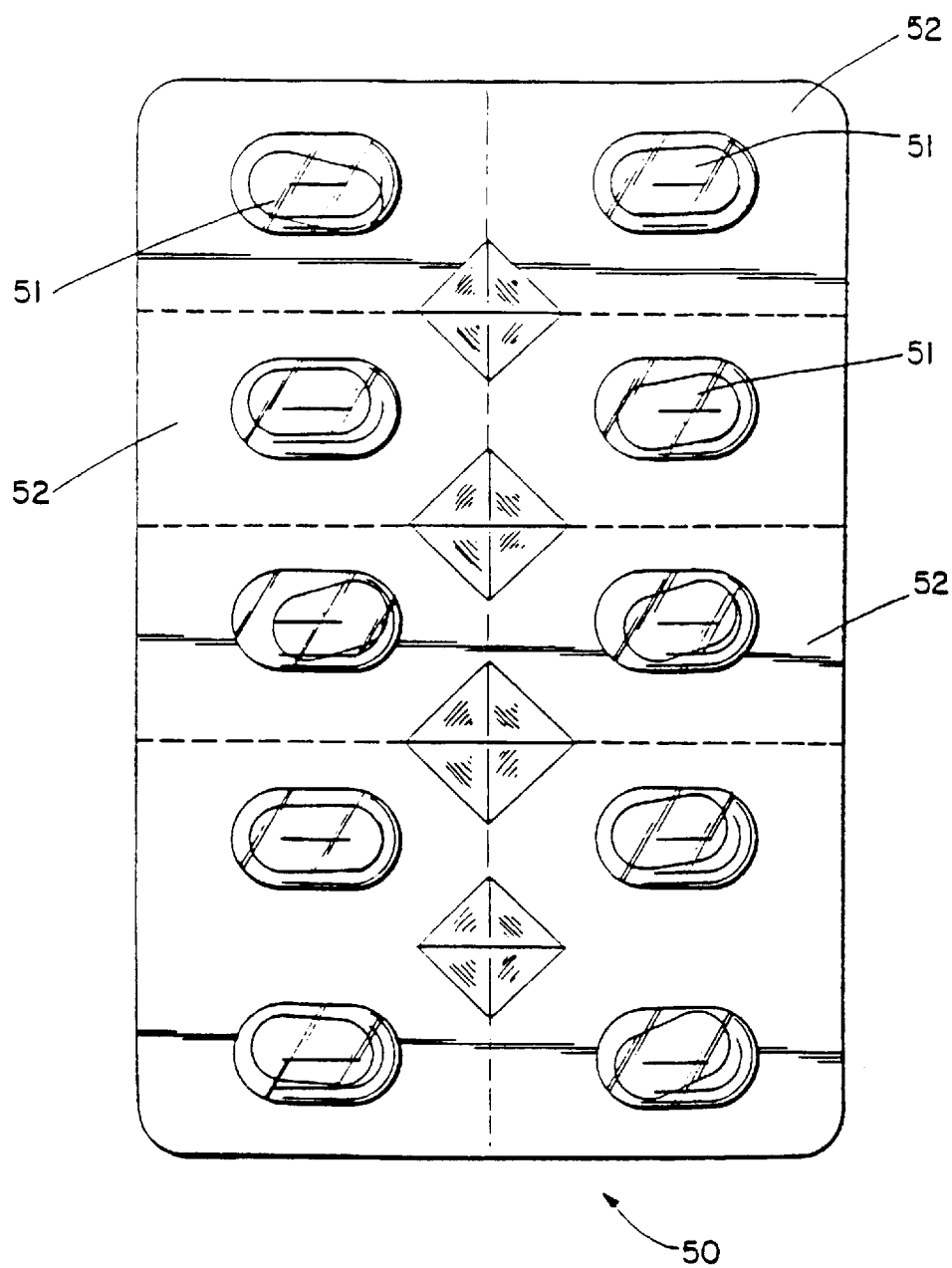
FIG. 3B shows an opposing side of the drug packaging card of FIG. 3A.
Figure 4:
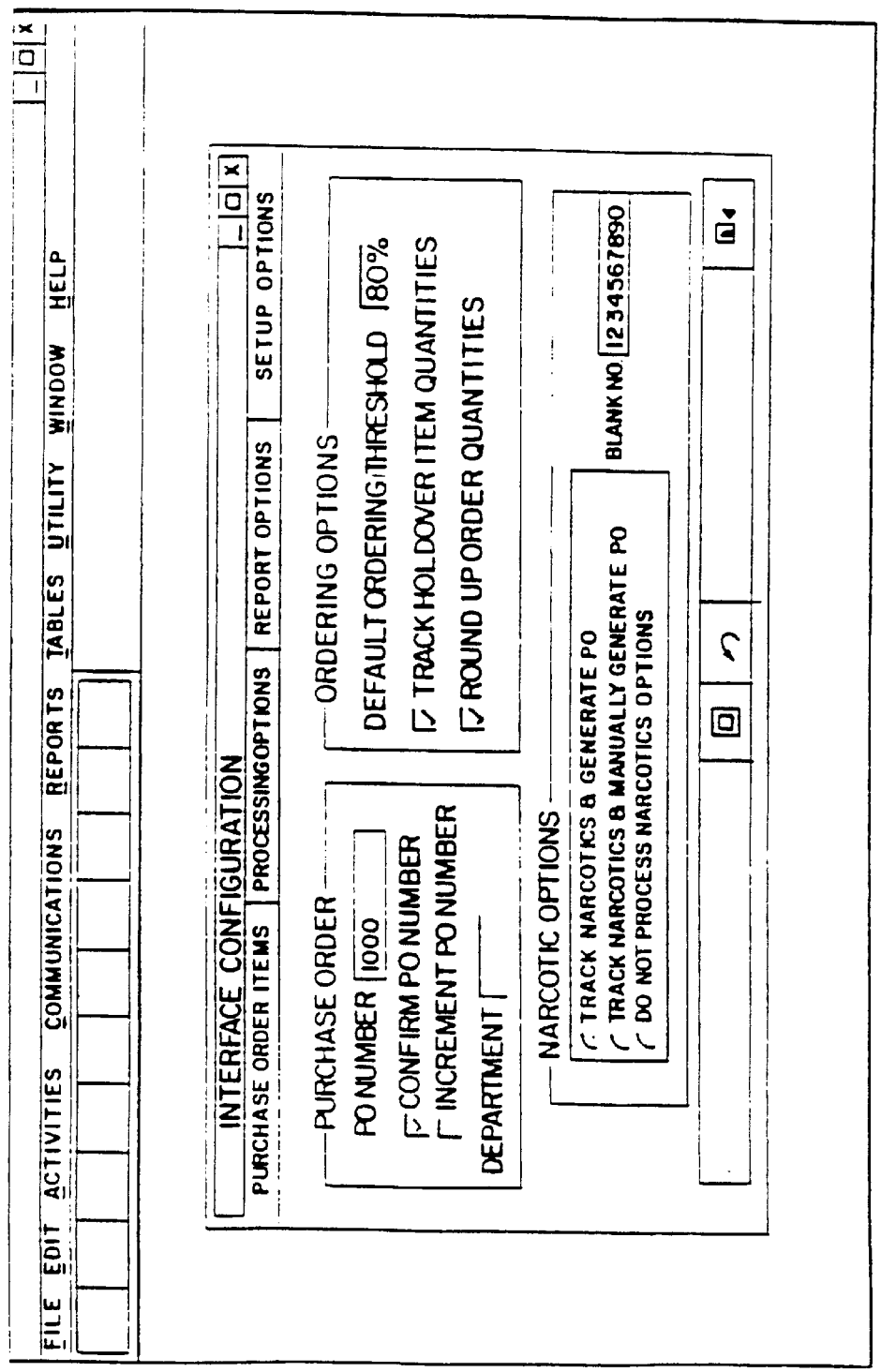
FIG. 4 shows an example of a preferred processing interface configuration of the computer software system of the present invention.
Figure 5:
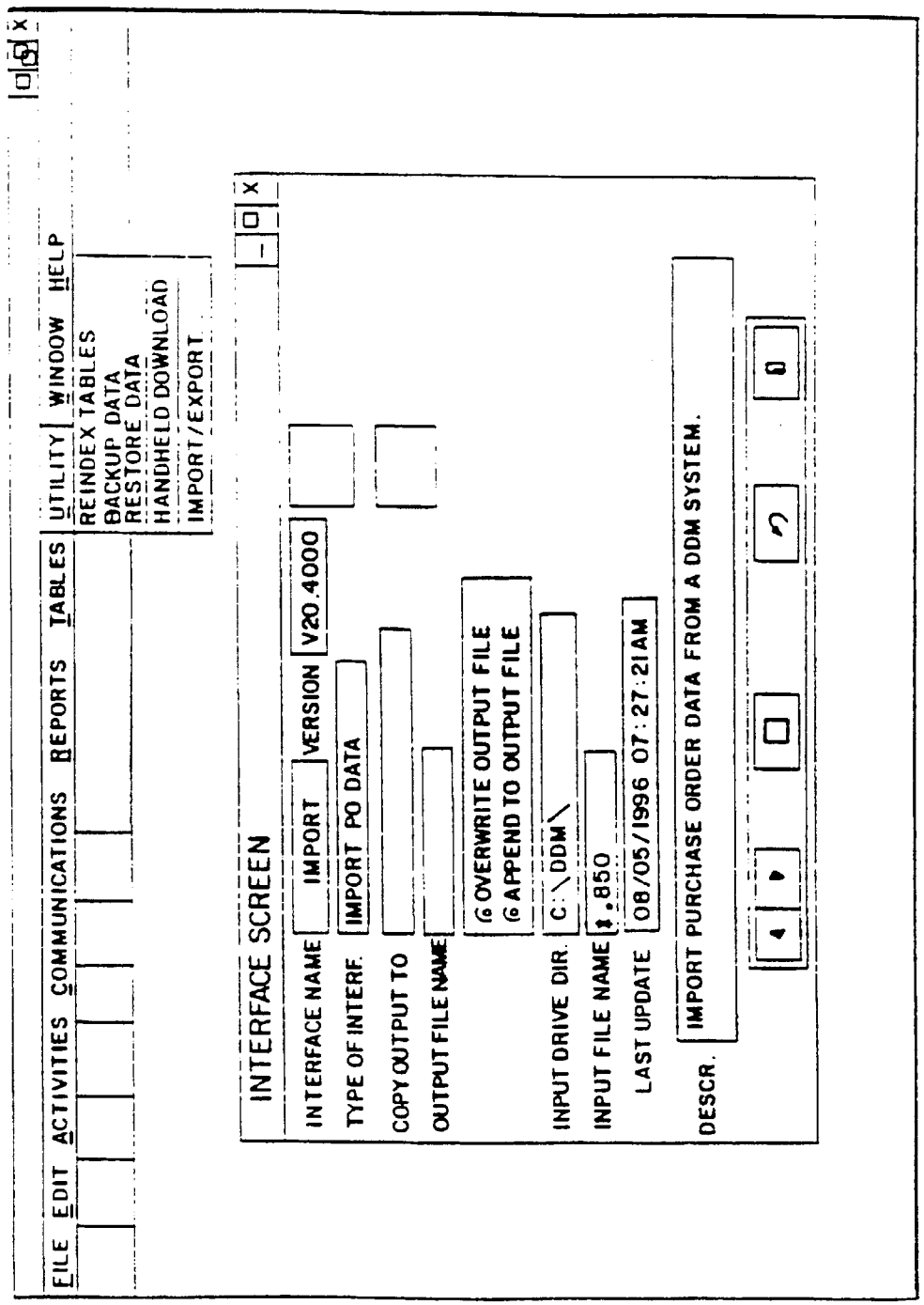
FIG. 5 shows an example of a data interface screen of a preferred form of the computer software system of the present invention.

Referring now to the drawings, and particularly FIG. 1A, a preferred embodiment of the system of the present invention is shown. The system shown at 10 may typically have at least three areas of data tracking of drug distribution. A first area 12 is the drug distribution center which is usually at a remote site from the health care provider institution. At the drug distribution center or at a computer facility in association with the drug distribution center, the first software program may be installed on a personal computer or network server for facilitating drug distribution management of low unit dose measures of the present invention.

A second drug distribution management software program of the present invention is installed at the health care provider facility 14 (for example in the pharmacy department) or at a computer facility in association with the health care provider. A third area for use of the present invention is at the various nursing stations 16 within the health care facility, primarily at drug dispensing machines 18 located at nursing stations.

In its preferred form, the present invention includes electronic communication and data sharing between the drug distribution software program and the health care provider software program, as well as between the drug dispensing machine software and the health care provider software program. The communication between the drug dispensing machines and the health care provider's pharmacy software program of the present invention, may be accomplished through hard wiring the drug dispensing machines throughout the facility to a central computer 20 operating the pharmacy second software program. Communication between the drug distribution center program of the present invention and the health care provider software program of the present invention may be accomplished via modem 22 and interface software running at each site as further described below. The interface may be, for example, a UNIX gateway. Since the distribution center may serve more than one health care provider in its region, each health care provider would be equipped to enter the distribution center computer system. This may involve having a gateway at the health care provider and another at the distribution center for gateway to gateway communication. Various other ways of setting up the communication link between the health care provider and the distribution center would be apparent to those of ordinary skill in the art when made aware of the contents of the present specification.

In accordance with a preferred embodiment of the present invention, several drug dispensing machines 18 within a health care facility 14 are in communication with the health care facility's central pharmacy computer ("CPC") 20 which is running the drug inventory management software program ("DIMS") of the present invention. Each drug dispensing machine ("DDM") may be uniquely identified by an identification code stored in the memory of the CPC. Each DDM may have a plurality of drawers, and pockets within each drawer, for storing certain drugs for later administering to patients. The DDM's identification code preferably includes information about the DDM's physical location within the health care facility.

The pharmacist may arrange to stock each DDM with particular drugs in particular drawers as well as in particular pockets within each drawer. Each DDM preferably includes data entry means such as a keypad to enable nursing staff to enter when a particular drug is administered to a patient, what drug was administered, what quantity was administered, and to which patient. Once entered into the DDM this information is automatically received by the CPC and utilized in DIMS running at the health care facility CPC.

Once the CPC receives the drug administering information from the plurality of DDM's, this information may be sent by the CPC to the drug distribution center computer ("DCC") also running a version of DIMS. It is important to note at this point that the DIMS running at the DCC and the DIMS running at the CPC may be the same program installed at multiple sites or it may be two separate programs adapted to communicate with each other. In either case, the CPC DIMS is adapted to track quantities and varieties of drugs received and administered to patients, and the DCC DIMS is adapted to track quantities and varieties of drugs shipped to particular health care providers and the remaining drugs those health care providers have purchased but which have not yet been requested for shipment to the health care facility. The DCC DIMS is also preferably adapted to produce an invoice to the health care provider for bulk drug purchases.

The software DIMS of the present invention is adapted to account for low unit dose measures of drugs. Unlike the drug distribution systems of old which accounted for bulk purchases but offered little or no low unit dose tracking, the present invention is especially designed to enable health care providers to reduce their own inventory of drugs and shift inventory management responsibilities to the drug distribution center. In this manner, the health care facility only receives those drugs that it will use in a relatively short period of time, thus substantially reducing inventory management responsibilities at the health care facility. Each health care facility would establish its own comfort level of drugs on hand and order from the drug distribution center accordingly. With the electronic communication between the DDM's and the CPC, the health care facility would have daily (or more frequently if desired) reports of drugs on hand at each DDM.

It should also be noted here that both the CPC and the DCC roles could be outsourced to third parties 24 in whole or in part, and still accomplish the intended purpose of the present invention. Furthermore, various programs may be written in various computer languages and formats to accomplish the roles of the CPC, DCC, and DDM data processors. Those specific programs and equipment described herein are not to be interpreted as limiting the broad scope of the present invention.

Another unique aspect of the present invention is the manner in which the low unit dose quantities of the drugs are packaged for delivery to each health care facility. In one embodiment of the present invention, a small plastic bag 30 is used as a package for unit dose measures of a drug. The individual doses of the drug may be contained in well known blister packs and placed in the plastic bag in predetermined quantities. The plastic bag may then be sealed with a perforated edge for later easy opening by health care providers. The plastic bags may be readily placed within the drawers of a DDM.

Prior to placing a drug in a plastic bag as described above, the bag may be printed on a face 32 thereof, with certain FDA required information. For example, the drug manufacturer's lot number 34, the variety of the drug 36, and the expiration date 38 of the drug may be printed or otherwise placed on the plastic bag. In addition, in a preferred embodiment of the present invention, certain of this information may be printed on the bag in the form of bar codes. With the use of bar codes there is less chance of human data entry errors when compared to manual data entry. Also, bar codes are faster to scan and thus enter into the DCC, CPC and DDM.

Using for example a low unit dose plastic package 30 in accordance with the present invention, containing a bar code 40 for expiration date of the drug, the system of the present invention offers a relatively fast system for tracking drugs that need to be removed from the DDM's. If a drug has expired, the CPC may inquire of the expiration dates of all of the drugs within a DDM (which in accordance with the present invention were earlier scanned and entered into the DDM). If expired drugs are shown to be present, the CPC will know exactly which DDM contains the expired drugs by referring to the DDM identification code. Thus, tracking of expired drugs for removal is handled electronically rather than manually checking each drawer of each DDM.

Likewise, lot numbers 42 and drug identification information 44, as well as other information may be placed on the bag in bar code form. Bar code scanners 45 may be located at each site 12, 14.

In another embodiment of the present invention a small paperboard card 50 serves as the drug packaging for low unit dose measures. The card is preferably of a size that enables it to be placed in a pocket of a drawer of a DDM. The card contains unit doses 51 of drugs in separate blister packs 52 attached to the card at perforated seems. The card may also contain bar coded information 54 as explained above.

In accordance with a preferred embodiment of the present invention, the CPC generates an electronic purchase order which is sent to the DCC. The purchase order contains a request for a bulk purchase of one or more varieties of drugs and also may include a request that only a certain lesser quantity than ordered be delivered at the present time. The DCC acknowledges the purchase order and fills the requested order. The DCC also tracks what quantities of the drugs ordered remain in inventory at the distribution center awaiting shipment upon request by the CPC. The DCC produces an invoice for the bulk order and sends the invoice to the CPC.

In a preferred embodiment, the distribution center ships the requested unit dose packages of drugs in "totes" (shipping containers) 60 which are predesignated for a particular DDM at the health care facility. Therefore, instead of the health care facility having to spend resources on getting the right drugs to the right DDM, the DCC can accomplish this in a much faster manner through its tracking of data received from the CPC (which received its data, in part, from each DDM) and the subsequent shipping of predesignated and properly labeled totes. The outside of each tote may also contain bar code information for easy tracking of totes as they are received at the health care facility.

The DIMS may be a Windows based program. The bar coding may be accomplished by commercially available bar coding equipment. The plastic bags and paperboard cards may be obtained from suppliers of similar packaging.

EXAMPLE CPC, DCC AND DDM SOFTWARE CONFIGURATION AND OPERATION STEPS FOR INTERFACING

1. Confirm that DDM system is set up with the CPC and in communication with the DCC. Within the DDM system, the interface may be configured with the following settings:

a. Set to Stockless—ordering information is broken down at the item level per station.

b. Set to Usage Net Vends—ordering quantities are based on the amount dispensed since the last time PO generated.

2. Match the DDM numbers used to identify items with the corresponding DCC item numbers.

3. Load either the DDM item numbers into the DCC or load the DCC item numbers into DDM.

Steps

1. Access the interface from the Import/Export option located off the utility menu in DCC.

2. If more than one interface is installed, operator may need to click on the next or previous arrows in order to locate the DDM interface.

3. Select the DDM interface as depicted below:

4. Specify the location of the incoming files. To specify the drive and directory where the incoming file(s) resides, click the mouse on "Input Drive/Directory" and a screen will come up allowing operator to select a path. Or operator may type in the desired drive and directory. If operator does not specify an incoming path, the interface defaults to searching for incoming files in the DCC system directory. If none are found, the interface will terminate processing.

5. "Input File Name" may be set to—*.850

6. Save changes by clicking on the save button (disk icon).

7. To configure the interface, click on the configuration button (wrench icon) and this brings up the following screen:

Purchase Order Items

This screen will be explained within the "Running the Interface" section of this guide. To continue with the setup and configuration, click the Processing Options tab.

Processing Options

Initially, fields set with default system settings.

1. Purchase Order Settings

PO Number—This is the purchase order number assigned to the incoming DDM order. The purchase order number may 12 alphanumeric characters.

Confirm PO Number—If selected, the following screen will be displayed before an order is created within the DCC system for each incoming DDM order. The screen displays the purchase order number that will be associated with the incoming DDM order.

Confirm whether or not operator wants to use this purchase order number. Operator may reset the number by typing in a new one and then select continue (rocket icon). The newly entered purchase order number is assigned to the incoming DDM order.

Increment PO Number—If selected, the purchase order number will automatically be incremented during processing. Once selected, specify the incremental value for the purchase orders.

Department—Enter the department code associated with the items on the incoming DDM order. This department code may be associated with all items on the order. Leave blank if operator does not want to assign a department code to the ordered items.

Ordering Options

Default Ordering Threshold—Percent of ordering unit met before item is ordered. This field sets the ordering level for all items. The ordering threshold must be met or exceeded for an item to be ordered. For example, if the threshold is set at 80% for a 100 count bottle of Tylenol, the interface will not place an order until at least 80 tablets have been requested from the DDM system. The ordering threshold value may be stored in the UDF2 field within Item Maintenance.

Track Holdover Item Quantities—By activating this field, the interface will carry over the extra quantity of a particular item or the quantity of an item that did not meet the ordering threshold and use it when calculating the next purchase order quantity.

Continuing from the above example, say only 80 Tylenol tablets were requested from the DDM. However, the hospital was shipped a 100 count bottle. The hospital received twenty additional tablets. The interface will track the additional tablets, and when the next request for that particular Tylenol comes through, the interface will subtract the 20 tablets from the requested amount. It is this adjusted value that will be compared to the ordering threshold.

Another scenario where this setting comes into play occurs when the Tylenol order is for 20 tablets. This does not meet the ordering threshold, so the item is not ordered. These 20 tablets will carry over and be added to the next request for Tylenol.

If this field is not activated, the carry over quantities are not tracked and each request is evaluated on an individual basis. It is recommended to activate this option.

Round Up Order Quantities—Round calculations up to the next ordering unit. For example, if activated and an order for 135 Tylenol tablets comes across, the interface would order two 100 count bottles.

Narcotic Options

Select one option

Track Narcotics & Generate PO—The interface will generate a purchase order for narcotic items that are ordered by the DDM system. If selected, enter the Blank Number in the available space.

Track Narcotics & Manually Generate PO—The ordered quantities for narcotic items will be tracked within the interface, but a purchase order will not automatically be generated for these items. These items will be tracked until a purchase order for narcotic items is manually requested. There is a mechanism for generating this purchase order on the Purchase Order Items screen. The "Running the Interface" section offers manually triggering a purchase order for narcotic items.

Do Not Process Narcotic Items—All orders for narcotic items are ignored by the interfaces. Ordering narcotic items for the DDM system is handled outside this interface. To save changes click on the save button (disk icon). Continue with the setup and configuration by clicking the Report Option tab.

Report Options

Report Setting

Print Order Exception Report when processing order—If activated, the Order Exception Report will automatically be generated and printed, if appropriate, while the incoming DDM order is being processed. Continue with the setup and configuration by clicking the Setup Options tab.

Setup Options

I. Cross-Reference Method

Denote whether DCC item numbers are matched up and stored in the DDM alternate ID field for all items, or whether the DDM item numbers are matched up with their corresponding DCC item numbers and stored within the DCC system.

If DDM item numbers are stored in DCC, the following will be displayed.

II. DDM Item # Found In

Identify in which field the DDM item numbers are stored within the DCC system. Both the "Stock Number" and the "UDF1" fields are accessible through Item Maintenance. At this point setup and configuration are complete, and the system is ready to import purchase orders from the DDM system.

Running the Interface

Steps:

1. The interface is run from the Import/Export option located off the utility menu in the DCC.
2. Select the DDM interface.
3. Adjust "Input Drive/Directory" as needed.
4. Save changes by clicking on the save button (disk icon).
5. To execute the interface, click on the launch button (rocket icon). The DDM order will be imported into the DCC. The interface will accumulate the item quantities across stations into one purchase order. If there are multiple purchase order files from the DDM, all items and order quantities will be consolidated into one purchase order within the DCC.
6. The interface will notify operator upon completion.
7. When processing has finished, review the incoming order within the Purchase Order section of DCC.
8. Also, there is a separate screen within the configuration portion of the interface for reviewing purchase order items and for tracking carry over quantities. This is accessed from the main DDM interface screen. To bring it up, click on the configuration button (wrench icon). The following screen appears:

Purchase Order Items

I. Item Grid

All items that have been ordered through the DDM system are listed. The main purpose of this grid is to allow review, and if necessary, adjustments to the carryover quantity and ordering threshold for a particular item.

Columns:

PO #*—the last purchase order that this item appeared on. If blank, the item was not ordered during the most recent processing or there is overstock of that particular item which keeps it from being reordered.

Item #*—DCC's item number for this product.

Description*—the trade name of the item as identified by the manufacturer.

Stock #*—the corresponding DDM item number for this product.

Class*—narcotic classification UOIF*—Unit Of Issue Factor—the number of units in the packaged product. Can be edited within Item Maintenance to reflect the number of unit doses contained within the package.

Track Qty—this is the carry over quantity associated with the item. A negative value represents overstock and that amount needs to be deducted before an order is placed. A positive value is the ordering quantity that has been accumulated to this point for the item. This value will be added to subsequent orders and compared against the ordering threshold. This column is highlighted because the value can be edited. Adjustments can be made to this field as deemed necessary.

Ord %—the ordering threshold associated with that particular item. This column is highlighted because the value can be edited. Adjustments can be made to this field as deemed necessary.

*—Fields can not be edited in normal browse mode. Only Item # and Stock # can be edited in ADD mode (plus icon).

II. Additional Features

Exception Override—there is capability to override an exception item status and order that item. In other words, if an item did not meet the ordering threshold, select that item and generate a purchase order for it.

Steps:
1. Tag the desired exception item(s). This can be accomplished two ways. One way is to select each item individually. Do this by marking the first column (*) with either the mouse or by hitting the space bar. The other manner for selecting exception items is to use the "Tag Exception Items for Order" option. Click the option button (check box icon). A list of options will appear. Select the "Tag Exception Items for Order" option and all exception items will be selected for the purchase order. Deselect an item by clicking on the selected check.
2. Select the launch button (rocket icon) to create a purchase order with the selected exception items.
3. Review the purchase order within DCC.

Adding Items—operator may add items individually to the table. Choose to do this if operator wants to preset the item with a unique threshold or tracking quantity.

Steps:
1. Click on the add button (plus icon) from the toolbar.
2. Fill in the appropriate data: DCC item number, stock number, track quantity, and threshold.
3. Click on the save button (disk icon) to save addition.

Narcotic Ordering—This feature is meant to be used in conjunction with the "Track Narcotics & Manually Generate PO" processing option. Order quantities have been tracked within the interface. When ready, operator may create a purchase order for the narcotic items.

Steps:
1. Tag the desired narcotic item(s). This can be accomplished two ways. One way is to select each item individually. Do this by marking the first column (*) with either the mouse or by hitting the space bar. The other manner for selecting exception items is to use the "Tag Narcotic Items for Order" option. Click the option button (check box icon). A list of options will appear. Select the "Tag Narcotic Items for Order" option and all narcotic items will be selected for the purchase order. Deselect an item by clicking on the selected check.
2. Select the launch button (rocket icon) to create a purchase order with the selected narcotic items.
3. Review the purchase order within DCC.

III. Screen Commands

Search—search for a specific item number, purchase order number, or stock number by typing in the desired number within the space provided. The area to enter the search values can be found above the command buttons.

Use the Tab key and/or the mouse to maneuver on the screen.

To exit the interface configuration, click on the exit button (exit door icon).

To delete an item record, click on the delete button (garbage can icon).

What is claimed is:

1. A system for drug distribution to health care providers, said system comprising:
   a first drug inventory management software program for a drug distribution center;
   a second drug inventory management software program for a health care provider facility computer;
   a third drug inventory management software program for a nursing station, said third software program in association with a drug dispensing machine;
   a low unit measure dose packaging including contents of a particular variety of drug, said packaging including at least one bar code whereby the information gathered from scanning said bar code is entered into said first and said second software programs; and
   a first communication link between said first software program and said second software program and a second communication link between said second software program and said third software program, said first and second communication links adapted to enable drug inventory information at said nursing station within said health care provider to be shared with said drug distribution center to enable said drug distribution center to have knowledge of drug quantity and variety needs at said health care provider.

2. The system of claim 1, wherein said bar code includes information pertaining to a drug manufacturer's lot number from which the drugs within said package were obtained.

3. The system of claim 1, wherein said bar code includes information pertaining to an expiration date of the drugs contained within said packaging.

4. The system of claim 1, wherein said bar code includes information pertaining to the type of drug contained within said packaging.

5. The system of claim 1, wherein said packaging is a sealed plastic bag containing at least one unit dose measure of a drug.

6. The system of claim 1, wherein said packaging is a paperboard card including a plurality of unit dose measures of a drug in blister packs attached to said card.

7. The system of claim 1, further comprising:
   a drug dispensing machine at said health care provider, adapted to receive said low unit measure package.

8. The system of claim 1, wherein said first drug inventory management software program tracks the total low unit measure quantities of drugs delivered to said health care provider and the balance of the quantity of drugs remaining from a bulk purchase of said drugs by said health care provider.

9. The system of claim 1, wherein said distribution center software is adapted to produce an invoice to said health care provider for a bulk purchase of said drugs.

10. The system of claim 1, wherein said first drug inventory management software program tracks drugs delivered to said health care provider, in low unit dose measurements.

11. The system of claim 10, wherein said first drug inventory management software program creates an invoice to said health care provider for drugs purchased in bulk.

12. The system of claim 1, wherein said drug distribution center maintains an inventory of drugs purchased by said health care provider and warehouses said purchased drugs at said drug distribution center while intermittently delivering purchased drugs to said health care provider in accordance with levels of need of said health care provider as indicated by said second drug inventory management software program.

13. A method for drug distribution to health care providers, said method comprising the steps of:

providing a first drug inventory management software program to be operated for a drug distribution center;

providing a second drug inventory management software program to be operated at a health care provider;

providing a third drug inventory management software program to be operated in association with a drug dispensing machine at said health care provider;

providing a low unit measure dose packaging including contents of a particular variety of drug, said packaging including a bar code indicating information about said contents;

scanning said bar code to thereby cause data from said bar code to enter at least one of said first program or said second program or said third program; and providing a first communication link between said first software program and said second software program and a second communication link between said second software program and said third software program, said first and second communication links to enable drug inventory information at said drug dispensing machine within said health care provider to be shared with said drug distribution center to enable said drug distribution center to have knowledge of drug quantity and variety needs at said health care provider.

14. The method of claim 13, wherein said first software program and said second software program are the same program operating at at least two locations.

15. The method of claim 13, wherein said first software program and said second software program are separate and distinct programs operating at separate locations.

16. The method of claim 13, wherein said first software program and said second software program are part of one central software program, said central software program operating at at least one location and in electronic communication with said first and said second programs.

17. The method of claim 13, wherein said bar code contains information relative to an expiration date of said drug.

18. The method of claim 13, wherein said bar code contains information relative to a manufacturer's lot number of said drug.

19. The method of claim 13, further comprising:

placing an order through said second software program;

receiving said order at said first software program;

delivering a first portion of said order to said health care provider;

maintaining a second portion of said order at said distribution center.

20. The method of claim 19, further comprising:

tracking drug inventory levels purchased by said health care provider, with said first software program.

* * * * *